United States Patent [19]
Sipin

[11] Patent Number: 5,759,148
[45] Date of Patent: Jun. 2, 1998

[54] CONTROLLED PNEUMATIC DRIVING SYSTEM

[76] Inventor: Anatole J. Sipin, 221 East 78 St., New York, N.Y. 10021

[21] Appl. No.: 543,262

[22] Filed: Oct. 18, 1995

[51] Int. Cl.$^6$ ............................................. A61N 1/362
[52] U.S. Cl. ........................................................ 600/18
[58] Field of Search ............... 600/16–18; 261/24–26, 261/30, 32; 222/36.1; 417/212, 213, 315, 429

[56] References Cited

U.S. PATENT DOCUMENTS

| | | | |
|---|---|---|---|
| 3,698,381 | 10/1972 | Federico et al. | 600/18 |
| 4,016,871 | 4/1977 | Schiff | 600/18 |
| 5,217,430 | 6/1993 | Mushika | 600/18 |
| 5,300,017 | 4/1994 | Isoyama et al. | 600/18 |

*Primary Examiner*—Jennifer Bahr
*Assistant Examiner*—Samuel Gilbert
*Attorney, Agent, or Firm*—Hedman, Gibson & Costigan, P.C.

[57] ABSTRACT

The invention is a system for inflating and deflating an intra-aortic balloon through an isolating safety chamber, which utilizes a flexible element to separate the balloon actuating gas from the driving air in a closed balloon circuit. Pressure and vacuum are supplied by separate pressure and vacuum stages, which are driven by the same shaft. The shaft speed is varied to control one of the pressures at a selected value, whereby the other pressure is maintained at a constant value within an allowable band.

15 Claims, 11 Drawing Sheets

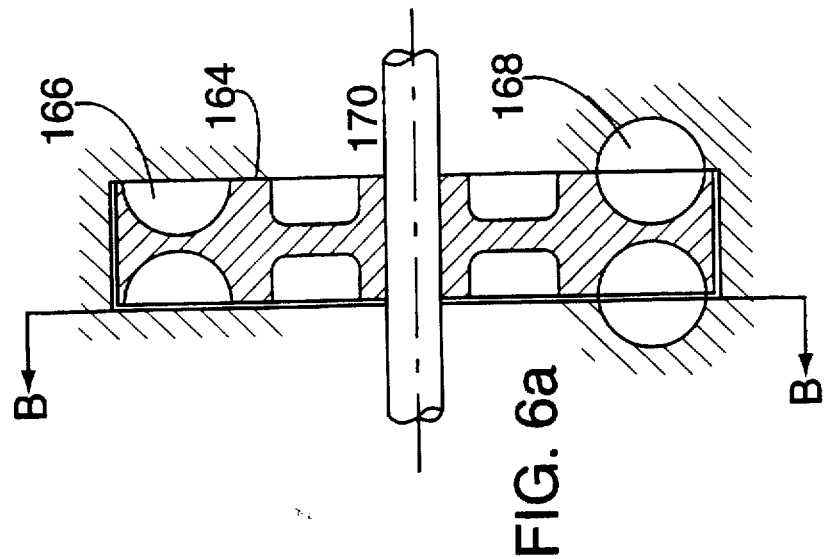
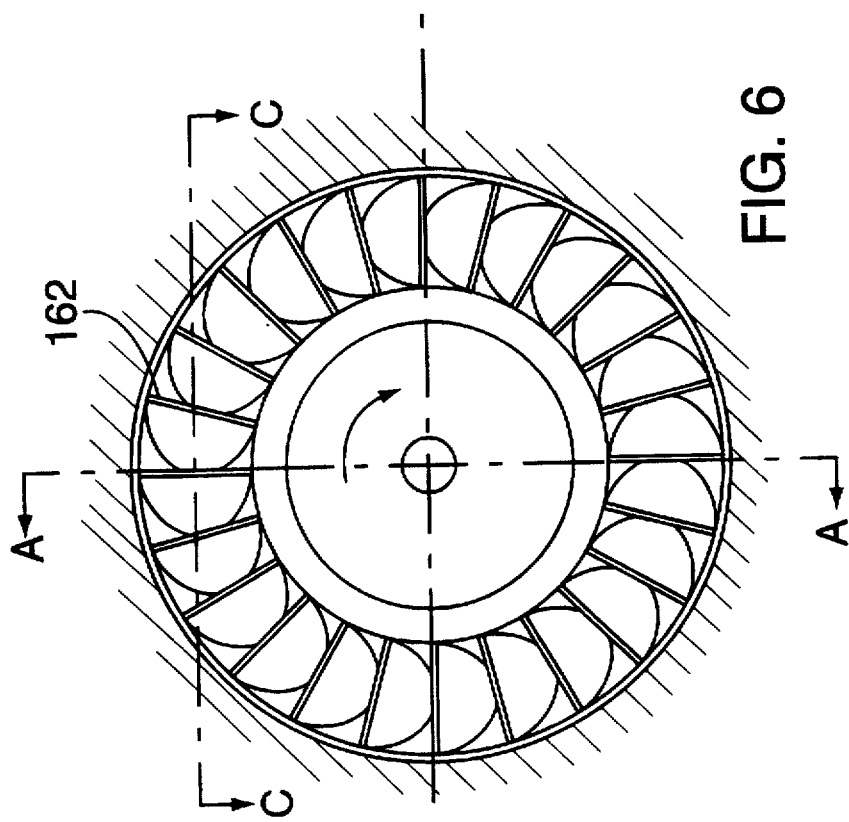

CONTROLLED PNEUMATIC DRIVING SYSTEM

BACKGROUND OF THE INVENTION

This invention relates to an improved controlled pneumatic driving system to be used for inflating and deflating a gas-filled intra-aortic balloon through an isolating safety chamber.

For a number of years the need for circulatory assist devices for use in cases of both acute and chronic heart failure has been recognized. There has been an increasing development and availability of such devices. In cases of acute myocardial infarction and for postcardiotomy patients who cannot be weaned from cardiopulmonary bypass, this type of immediate temporary assist is required. Since more than 30 years ago, the efforts of Kantrowitz, Clauss, Mouloupolous, Kolff and Topaz have resulted in the now widely used counter-pulsation intra-aortic balloon pumping (IABP), which increases myocardial oxygen uptake and coronary perfusion, and reduces load on the heart and its oxygen demand.

Balloon pump driving consoles have been designed for clinical use in hospital operating rooms and intensive care units. They are relatively large and heavy, ranging in weight from 100 to 200 lbs. There is a need for a small and lightweight balloon pump driver that weighs 30 lb. or less and that can be carried and applied by a single person. Such a unit would be useful for inter and intra-hospital transport, and the small size and weight would be advantageous for ease of clinical use as well. A portable driver could also be less expensive than a larger console, giving it a competitive advantage for clinical as well as transport use.

Previous attempts to provide a portable intra-aortic balloon pump driver have accomplished reduction in size and weight of existing clinical drivers, but with the resulting units more properly described as movable rather than easily portable. Such "transport" units have been made by Kontron and Datascope, but the weight is in the area of 100 lbs. Bard has introduced a smaller clinical driver with a specified weight of 57 lbs., but it cannot be carried by a single individual.

A preliminary design has been generated for a portable balloon pump driver that includes a Pneumatic System containing a miniature, combined drag type compressor/vacuum pump that is driven by a single motor, and a miniature double-acting directional valve; a miniaturized Electronic Control System that contains a microcomputer and an ECG/AOP trigger circuit, a Helium Fill System that is capable of balloon refilling every two hours for 48 hours, and that contains a small helium bottle and a miniature regulator; an Electric Power System that contains two small power supplies and a DC-to-DC converter to supply the 24 V DC system voltage from an automotive supply (12 V DC), an aircraft supply (28 V DC) or 110 V AC mains; and that also contains a one-hour rechargeable battery plus a one-hour emergency battery that is non-rechargeable and a Display System that uses a very small digital monitor. The unit measures 9.25 in. W×9.75 in. H×16 in. L, with a displaced volume of 0.84 cu.ft. The weight is 27.0 lbs. without a safety chamber and 28.0 to 30.0 lbs. with a safety chamber.

SUMMARY OF THE INVENTION

The invention is a controlled pneumatic driving system, whose primary application is inflating and deflating an intra-aortic balloon through an isolating safety chamber, connected in series with the balloon, that contains a flexible element to separate the driving fluid from the balloon inflating fluid, and to transmit pressure between the two fluids. The system consists of a fluid load, such as an intra-aortic balloon, a pressure pump to deliver fluid to the load under positive pressure, a suction or vacuum pump to remove fluid from the load under reduced pressure, that could be vacuum, and that has a characteristic performance that varies with speed in a manner similar to the pressure pump, and means to drive the pressure pump and the suction pump at the same speed.

The system also provides means to control one of the pressures, whereby the other pressure will be at a known value within an allowable band. The control means includes means to select a value of the controlled pressure, means to measure the actual value of the controlled pressure, means to compare the selected and actual pressures, having an output related to their difference, and means responsive to the differential output of the comparator means to vary the drive speed in a direction and by an amount to reduce the differential output to a minimum, so as to maintain the controlled pressure at its selected value, and the other pressure at a constant value within an allowable band. Reservoirs or accumulators are connected between the pumps and the load to reduce pressure fluctuations and pump flow rate requirements.

BRIEF DESCRIPTION OF DRAWINGS

FIGS. 6, 6A, 6B, and 6C are diagrams showing features and operation of a typical drag compressor.

DETAILED DESCRIPTION OF THE INVENTION

Figure 1:
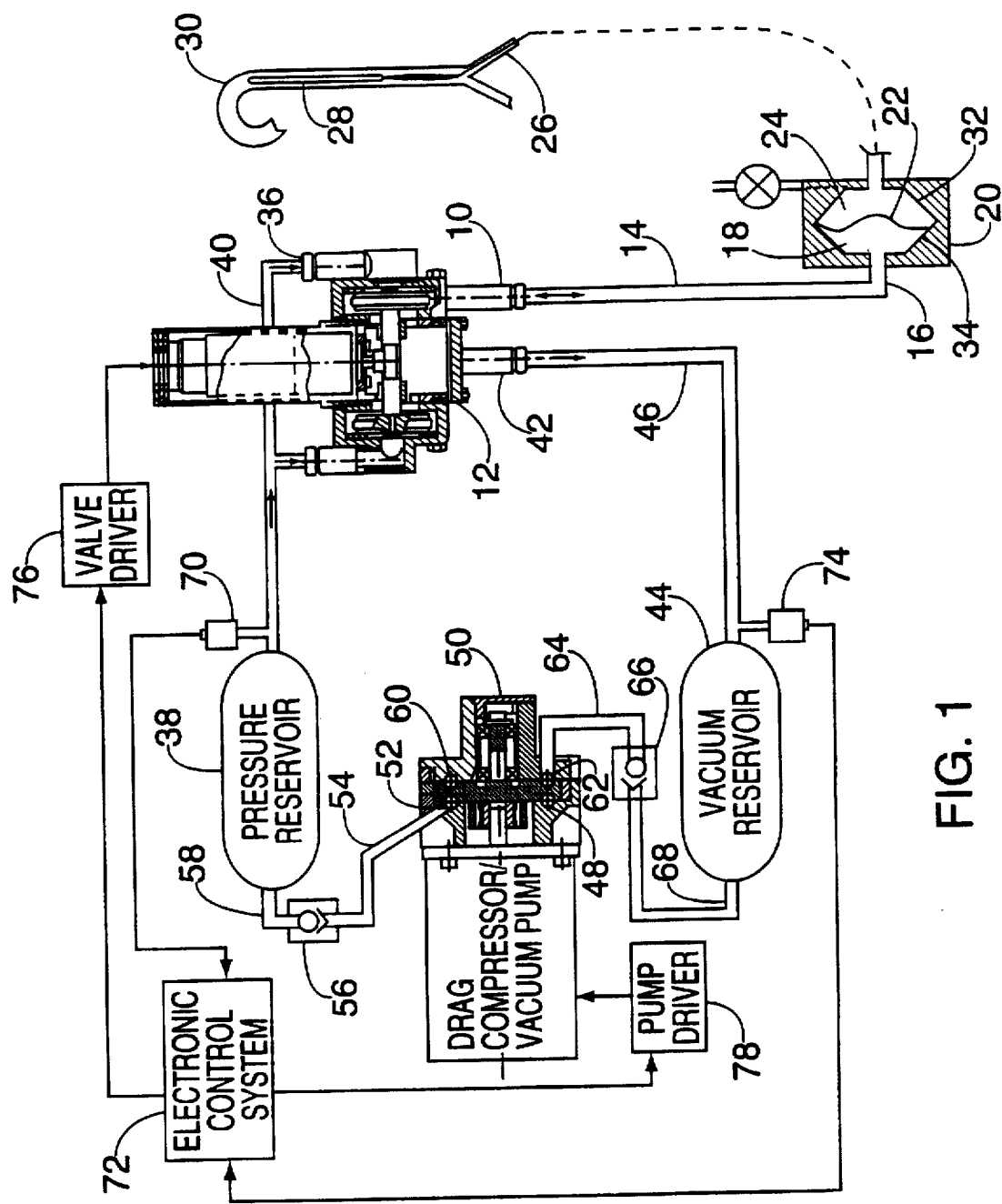
FIG. 1 is a schematic diagram of the pneumatic driving system, arranged for inflating and deflating an intra-aortic balloon catheter through a safety chamber.

FIG. 1 is a general arrangement of the preferred embodiment of the controlled pneumatic driving system for inflating and deflating an intra-aortic balloon catheter through an insulating safety chamber, which utilizes a slack diaphragm to separate the helium from the pressurized air in a closed balloon circuit. The balloon is inflated and deflated through pressurization and de-pressurization by air of the diaphragm, and pressure transmission through the diaphragm between the air and the helium. During balloon inflation, air under pressure is applied from driving port 10 of balanced motor-driven double-acting valve 12, through line 14, to port 16 and air cavity 18 of safety chamber 20, to pressurize slack diaphragm 22. The diaphragm flexes, compressing helium in helium cavity 24, and driving the helium through catheter 26, which has been inserted intracorporeally through a major artery, to inflate balloon 28, which has been placed within the descending aorta 30 for cardiac assist of a patient. The diaphragm continues flexing and expanding the balloon until the diaphragm seats against the wall 32 of safety chamber 20, at which time all of the helium is expelled and is contained within the expanded balloon. The bottoming of the diaphragm against the wall of the safety chamber protects the balloon from overpressurization by air. For deflation of the balloon, vacuum is applied through line 14 and driving port 10 of valve 12, de-pressurizing air cavity 18 to cause reverse flexure of diaphragm 22 until it seats against the opposite wall 34 of safety chamber 20. Helium is drawn by the vacuum in helium cavity 24 out of the balloon until it is completely deflated and the helium is returned to cavity 24. Pressurized air is continuously applied to pressure port 36 of valve 12 from pressure reservoir 38 through line 40, and vacuum is continuously applied to vacuum port 42 of valve 12 from vacuum reservoir 44 through line 46. Pressure reservoir 38 is continuously supplied by pressure stage 48 of combined rotary drag compressor/vacuum pump 50 through compressor outlet 52, line 54, pressure check valve 56 and pressure reservoir inlet 58; and vacuum reservoir 44 is continuously evacuated by vacuum stage 60 of compressor/vacuum pump 50 through vacuum pump inlet 62, line 64, vacuum check valve 66 and vacuum reservoir outlet 68. The reservoirs are of such a size (approximately 1 liter) that the volume of air required to pressurize or evacuate the safety chamber in each cycle causes an acceptably small change in the pressure or vacuum in the reservoir.

The outlet pressure from the pressure reservoir is sensed by pressure transducer 70, whose output is fed to micro-computerized electronic control system 72. The vacuum into the vacuum reservoir is sensed by vacuum transducer 74, whose output is also fed to electronic system 72. Electronic system 72 controls the actuation of double-acting valve 12 through valve driver 76, and it also controls the speed of compressor/vacuum pump 50 through pump driver 78 in order to maintain the desired system pressure and system vacuum. Since the pump speed affects the outputs of both the pressure and vacuum stages in the same direction, and there is only one degree of pump freedom, a novel scheme is used to control both pressure and vacuum, in which active control of one of the parameters provides inherent regulation of the other. Since the same flow passes through both stages, both pump stages are matched so that they vary proportionately with changes in beat rate or pulse frequency. This scheme permits the use of a combined pump rather than separate pumps, and eliminates need for a regulator, which could exact a weight and power penalty.

Electronic control system 72 modulates driving power to the compressor/vacuum pump motor to vary speed so as to maintain reservoir pressure and reservoir vacuum at selected values, in accordance with the control scheme described above. It also controls actuation of the motor-driven valve to apply balloon inflating pressure or deflating vacuum to the safety chamber in response to an external trigger or internally programmed signals at various selectable rates (e.g. 40, 60, 80, 100, 120 bpm) and different duty cycles (e.g. 65% inflation, 50% inflation, etc.). The control system includes a compressor/vacuum pump motor driving circuit and a driving circuit for the double-acting safety chamber valve. An electrocardiogram (ECG) and aortic pressure (AOP) signal acquisition and trigger circuit is included for initiation of deflation/inflation from the patient's heartbeat. The system is under the control of a microcomputer module, which also can be used for monitoring and control actuation.

Figure 2:
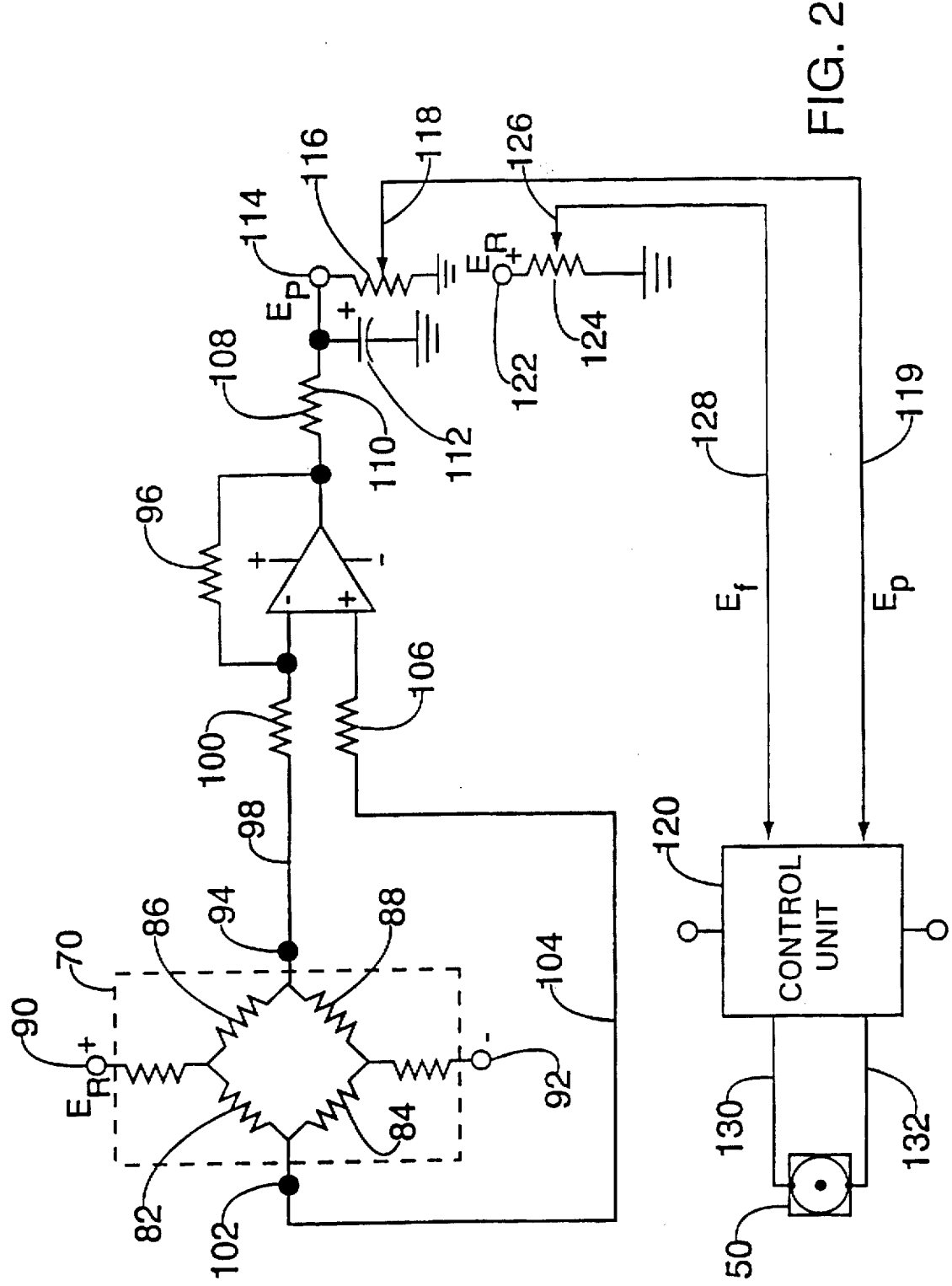
FIG. 2 is a schematic diagram of the pressure/vacuum control system.

A schematic diagram of a general embodiment of the constant reservoir pressure (vacuum) control system that corresponds to the system diagram of FIG. 1 is shown in FIG. 2. Pressure transducer 70 is here shown to be of the piezoresistive type, and it comprises active pressure sensitive resistors 82, 84, 86, and 88 connected in a bridge arrangement. A regulated voltage $E_R$ is applied at positive terminal 90 and negative terminal 92. Output terminal 94 is connected to an operational amplifier 96 through lead 98 and input resistor 100. Output terminal 102 is connected to operational amplifier 96 through lead 104 and resistor 106. Low pass filter 108, consisting of resistor 110 and capacitor 112 applies the amplifier output voltage to terminal 114 of pressure signal potentiometer 116. Reservoir pressure sensed by transducer 70 produces a voltage at terminals 94 and 102 that is fed to operational amplifier 96 to provide a voltage $E_R$ that is linearly related to the pressure on lead 119 to control unit 120, which corresponds, generally, to electronic control system 72 and pump driver 78 of FIG. 1.

Regulated voltage $E_R$ is also applied to terminal 122 of reference potentiometer 124, whose wiper 126 feeds a pressure reference voltage $E_r$ also to control unit 120 on lead 128. A motor drive voltage is fed from control unit 120 to the drive motor of drag compressor/vacuum pump 50 on leads 130 and 132.

Figure 3:
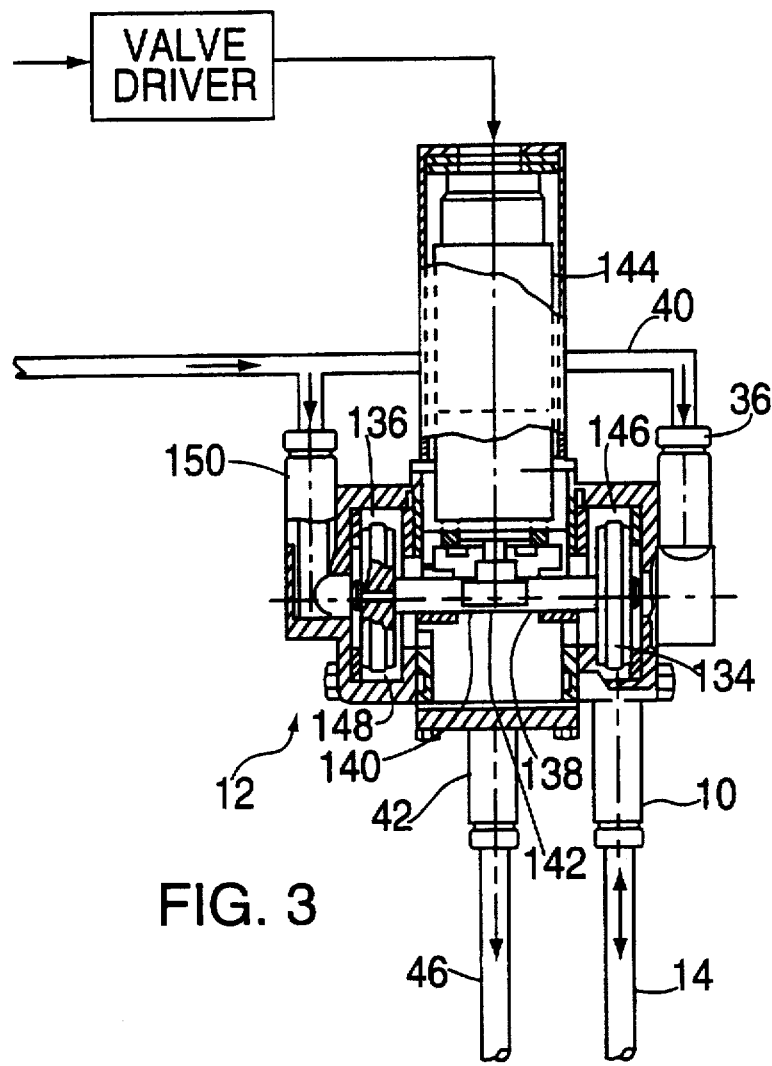
FIG. 3 is a drawing of a balanced, motor-driven, double-acting valve, that can be used in the system shown in FIG. 1.

Referring to FIG. 3, it is seen that balanced motor-driven double-acting valve 12 includes r.h. poppet 134 and l.h. poppet 136, that are mounted on opposite ends of shaft 138, which incorporates central toothed rack section 140, which meshes with gear 142 that is mounted on the output shaft of drive motor 144 of valve 12. Poppet 134 is reciprocated in chamber 146 that is permanently connected to safety chamber 20 and alternately exposed to pressure through port 36 and vacuum through port 42. In the extreme left position shown in FIG. 3, poppet 134 seals chamber 146 from vacuum, and pressure from line 40 is applied to safety chamber 20 through port 36, chamber 146, port 10 and line 14. In the extreme right position, poppet 134 seals chamber 146 from pressure, and vacuum from line 46 is applied to safety chamber 20 through port 42, chamber 146, port 10 and line 14. Poppet shaft 138 is cyclically reciprocated by drive motor 144 through gear 142 and rack section 140 between the two extreme positions, to alternately apply pressure and vacuum to the safety chamber. Poppet 136 is reciprocated in chamber 148, and its right face is continuously exposed to vacuum through port 42. Pressure and vacuum are applied to opposite faces of poppets 134 and 136, approximately balancing pressure forces on shaft 138 and minimizing the valve actuation load.

Figure 4:
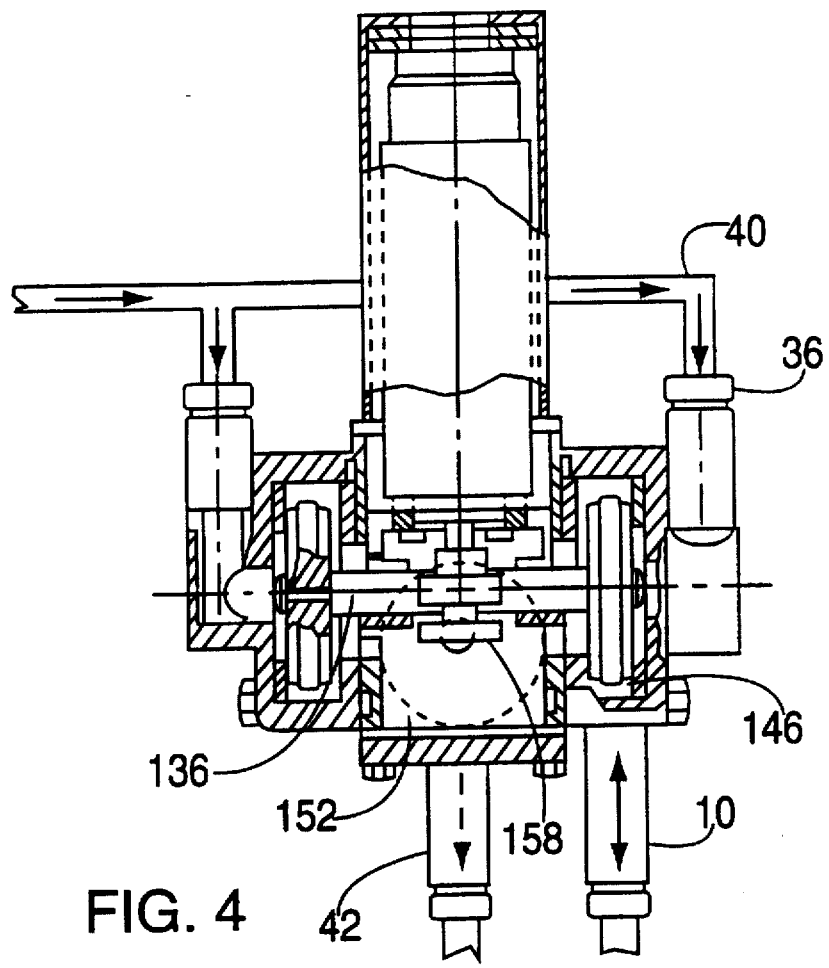
FIG. 4 is a drawing of the motor-driven, double-acting valve shown in FIG. 3, that incorporates a disc type, momentary, atmospheric dump valve.
Figure 5:
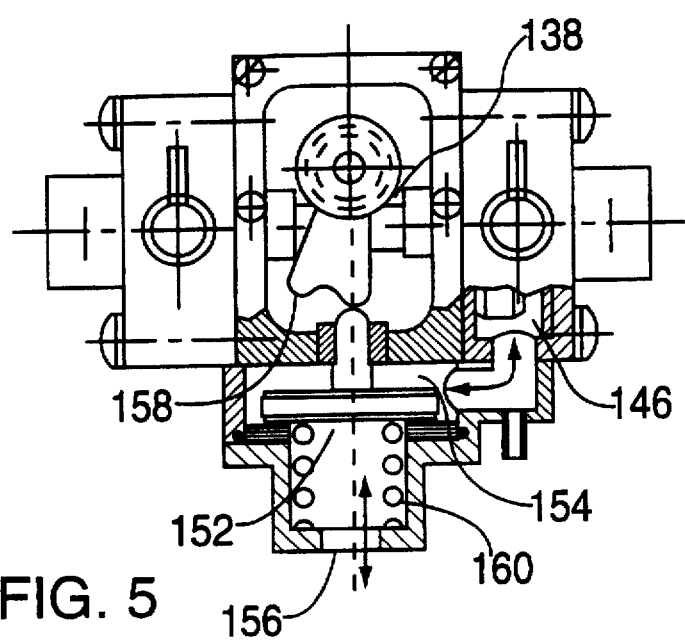
FIG. 5 is a partially sectioned bottom view, with the bottom cover removed, of the double-acting valve shown in FIG.4, illustrating momentary actuation of the dump-valve disc by a cam synchronized with the poppet drive shaft.

Pneumatic power expended by the compressor/vacuum pump can be reduced by momentarily exposing air cavity 18 of safety chamber 20 to atmospheric pressure during the transition from one pressure state to the other. This is accomplished by an auxiliary, spring-loaded poppet. Referring to FIGS. 4 and 5 it is seen that auxiliary poppet 152 rides in cavity 154, and in its normally closed position it seals cavity 146 from atmosphere through opening 156. Poppet 152 is kept closed at each of the extreme positions of shaft 138 by cam 158 against the face of spring 160. At the central position of shaft 138 the cam releases poppet 152, which is opened by spring 160, connecting cavity 146 to atmosphere through opening 156. In cyclic travel between the two extreme positions, where poppet 152 is closed, it is briefly opened by cam 158 to provide a momentary exposure of chamber 146 to atmosphere, improving pneumatic efficiency.

Figure 6C:
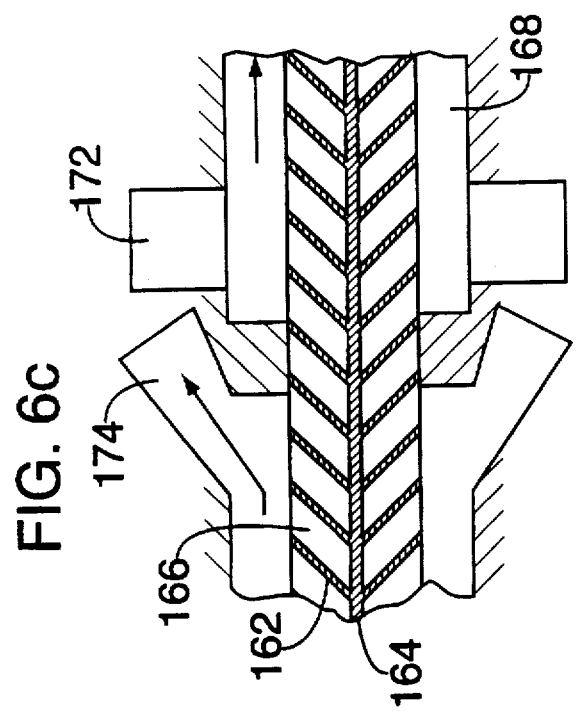
Figure 6B:
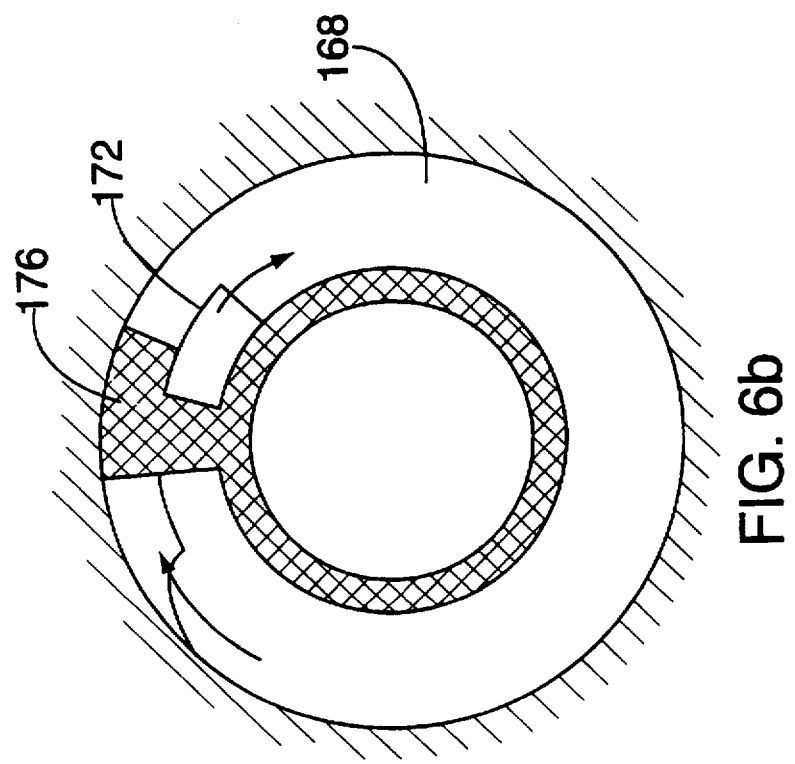

In drag pumps (also known as regenerative pumps and side channel pumps) air is driven by a rotating impeller through a stationary annular channel by a combination of viscous and dynamic effects. The operation is illustrated in FIGS. 6, 6A, 6B and 6C. FIG. 6 is a frontal view showing the geometry of the impeller. FIG. 6A is a side view along Section A—A, showing relations between the rotary and stationary flow channels. FIG. 6B is a view along Section B—B, showing the stationary channel, the inlet, the outlet and a blade seal between them. FIG. 6C is another view along Section C—C.

Radial vanes 162 are machined into the side of impeller disc 164 to form a circular row of cavities 166. These correspond with stationary annular channel 168, which is located in the side of stator 170, and which has a circumference less than 360 degrees. Air enters channel 168 through side inlet port 172, and it leaves through side outlet port 174 at the other end. Ports 172 and 174 are separated by block seal 176 in which area a very small clearance is maintained between impeller disc 164 and stator 170. As shown in FIG. 6C duplicate side channel (drag) pumps are frequently arranged on opposite sides of the impeller. These, however, are identical, and they are connected in parallel, so as to maintain the same pressure gradients on opposite sides of the impeller and minimize leakage across the periphery of the impeller, and also to reduce the diameter and speed required for a given output.

The flow in annular channel 168 is composed of circulation in impeller cavities 166 caused by centrifugal effects and circumferential flow caused by impeller rotation, producing a complex flow pattern that resembles a corkscrew motion wrapped around a cylinder. This produces a unique performance characteristic in which maximum pressure is achieved at zero flow rate. This causes the drag pump to be considered a hybrid between a dynamic pump and a displacement pump. Its characteristic is not as flat as that of a typical dynamic pump and not as steep as that of a typical displacement pump. Its specific speed is also somewhere between the dynamic pump and the displacement pump. Thus, typical applications are for cases where a dynamic pump would yield too high a rotative speed and where a displacement pump would have comparatively small dimensions which might be difficult to fabricate.

Figure 7:
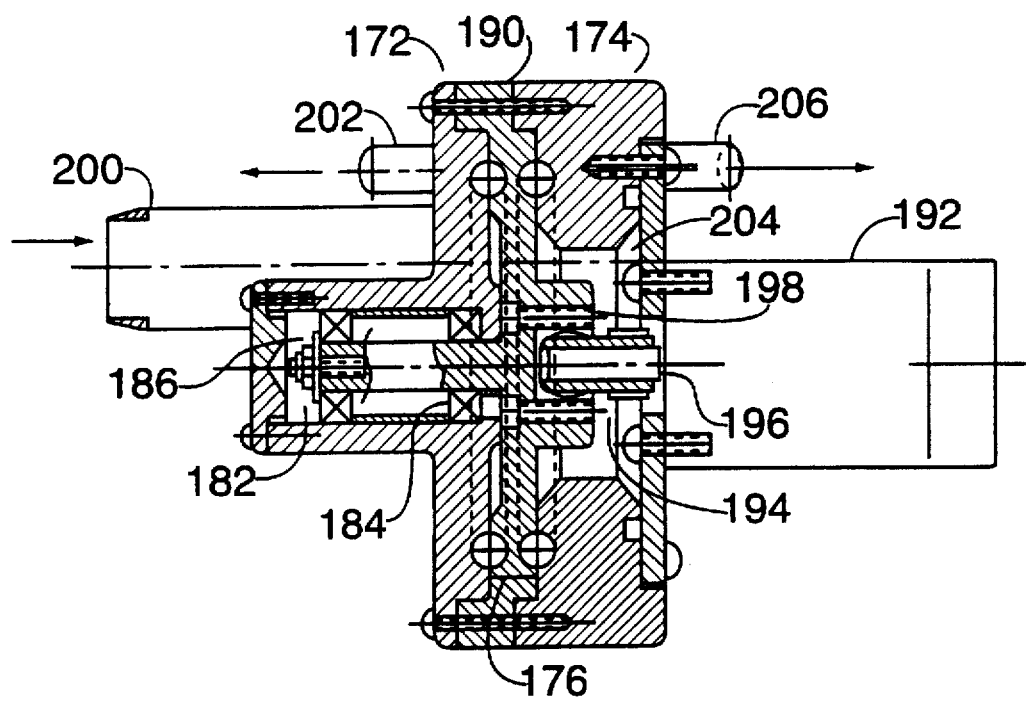
FIG. 7 is a sectional drawing showing construction of a single rotor drag pump with pressure and vacuum stages on opposite sides of the rotor.

A practical configuration for a combined drag compressor/vacuum pump, in which compression stage 172 and vacuum stage 174 are incorporated on opposite sides of single rotor disc 176, is shown in FIG. 7. The design differs from prior designs, that are illustrated in FIGS. 6, 6A, 6B and 6C, in that the design parameters, such as channel dimensions, number and angle of blades, etc., are different, being optimized for the compression design point of the compressor stage at the design speed of the single rotor, and optimized for the vacuum design point of the vacuum stage at the same rotor design speed. In the construction shown rotor disc 176 is operative with compressor stator 176 to form compression stage 172, and the rotor disc is operative with vacuum pump stator 180 to form vacuum stage 174.

Unlike other designs, where spring loading is used to take up axial play, the rotor bearings, here, are shimmed to eliminate the play with a minimum of bearing compression, so that there can be no axial motion due to pressure loading, and the bearing friction is minimized.

Rotor 176 is independently mounted on ball bearings 182 and 184 that are adjusted for zero axial or radial play by shim 186. Another shim, 188, sets the clearance of the front of the rotor (pressure stage) at the desired value (e.g. 0.001 in.). The vacuum stage is machined into the opposite side of rotor 176 and into vacuum stator 180. The vacuum stage clearance is determined by precision ring 190 whose width is machined to be greater than the width of the rotor by an amount exactly equal to the rotor pressure stage clearance (e.g. 0.001 in.). Motor 142 is a special high speed, brushless DC motor with special male spline 194 on shaft 196, that mates with female spline 198 in rotor 176, and an integral electronic commutator.

Air enters compression stage 172 from atmosphere through inlet 200 and exits under pressure through compression stage outlet 202 to the pressure reservoir. Air at a vacuum from the vacuum reservoir enters vacuum stage 174 through inlet 204 and exits to atmosphere through outlet 206. Unlike the conventional arrangement, which has identical compression stages on both sides of the rotor to eliminate an inter-channel pressure difference, the drag compressor/vacuum pump of FIG. 7 has a substantial pressure gradient across rotor 176 from the pressure stage to the vacuum stage. Leakage is minimized by controlling the axial tip clearance between rotor 176 and stators 178 and 180 at a minimum value (e.g. 0.001 in.), which eliminates the effect of radial clearance between the rotor external circumference and the inner circumference of ring 190 and makes that clearance non-critical.

Figure 8:
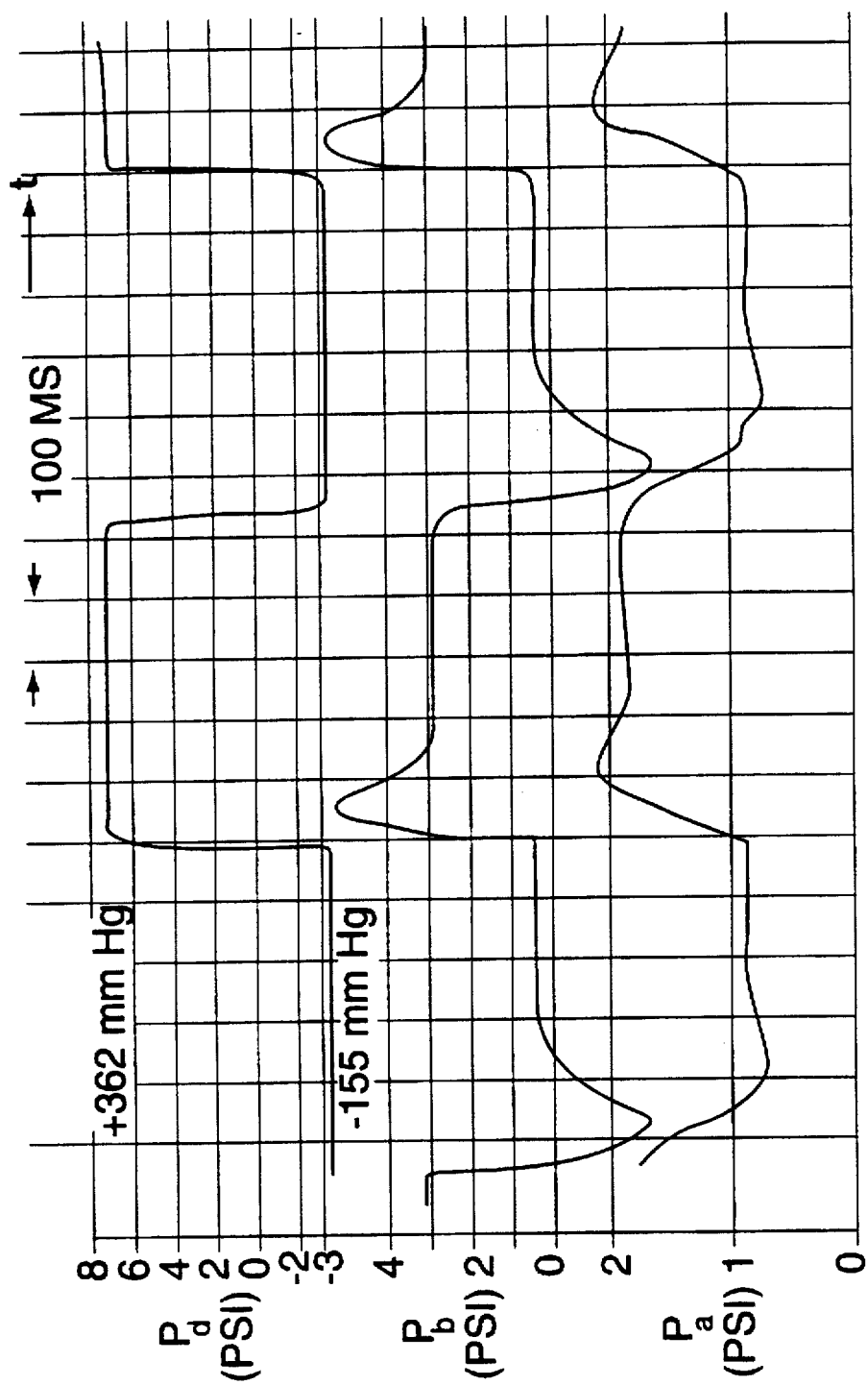
FIG. 8 is a test record of the cyclic response of an idealized intra-aortic balloon pumping system using very fast solenoid valves and infinite reservoirs.

A representative test recording for an experimental intra-aortic balloon pump drive is shown in FIG. 8. The data are for an idealized test system similar to that shown in FIG. 1, except that very large reservoirs (i.e. over 100 liters) were used to provide a substantially constant drive pressure, and the double-acting valve was replaced by two very fast (under 15 milliseconds) solenoid valves. $P_d$ corresponds to the driving air pressure at port 16 of safety chamber 20 in FIG. 1. $P_b$ corresponds to the helium pressure in cavity 24 of safety chamber 20. $P_a$ is air pressure within a burette enclosing an intra-aortic balloon, corresponding roughly to the change in pressure within aorta 30 caused by inflation/deflation of balloon 28. Balloon inflation time is defined as the time between the 10% and 90% points of the total increase in balloon chamber pressure, $P_a$, after application of a signal to the valve driver 76. Deflation time is similarly defined. In addition to fast application of driving pressure/vacuum ($P_d$), it is necessary that adequate levels of pressure/vacuum be maintained at an approximately constant value. The beat rate for the case shown in FIG. 8 was 60 beats/minute, and it is necessary that the applied driving pressure/vacuum remain the same at higher beat rates up to 150 beats/minute.

Conventionally, to maintain a constant pressure in pressure reservoir 38 and a constant vacuum in vacuum reservoir 44 with a control that varies pump speed, a two-degree of freedom control is required. That is, a separate motor-driven compressor, whose speed is modulated by a separate pressure control system, similar to that shown in FIG. 2, is used to control pressure in the pressure reservoir, and a separate motor-driven vacuum pump, whose speed is modulated by a separate vacuum control system, similar to that shown in FIG. 2, is used to control vacuum in the vacuum reservoir.

This requires two separate drives and two control systems and adds considerably to the size, weight and cost of an intra-aortic balloon pump driver, particularly a portable unit that is sufficiently small and lightweight to be carried and applied by a single individual.

It is the stated object of the invention that is here disclosed to achieve adequate regulation of both pressure and vacuum by speed variation of a single combined compressor and vacuum pump to achieve a size, weight and cost saving. Combined compressor/vacuum pumps have been used heretofore, but those have been of the diaphragm type driven by a single relatively large, and slow speed AC induction motor at approximately constant speed. Pressure and vacuum have been controlled by pneumatic regulators or relief valves, which waste energy at demands lower than the maximum.

Figure 9:
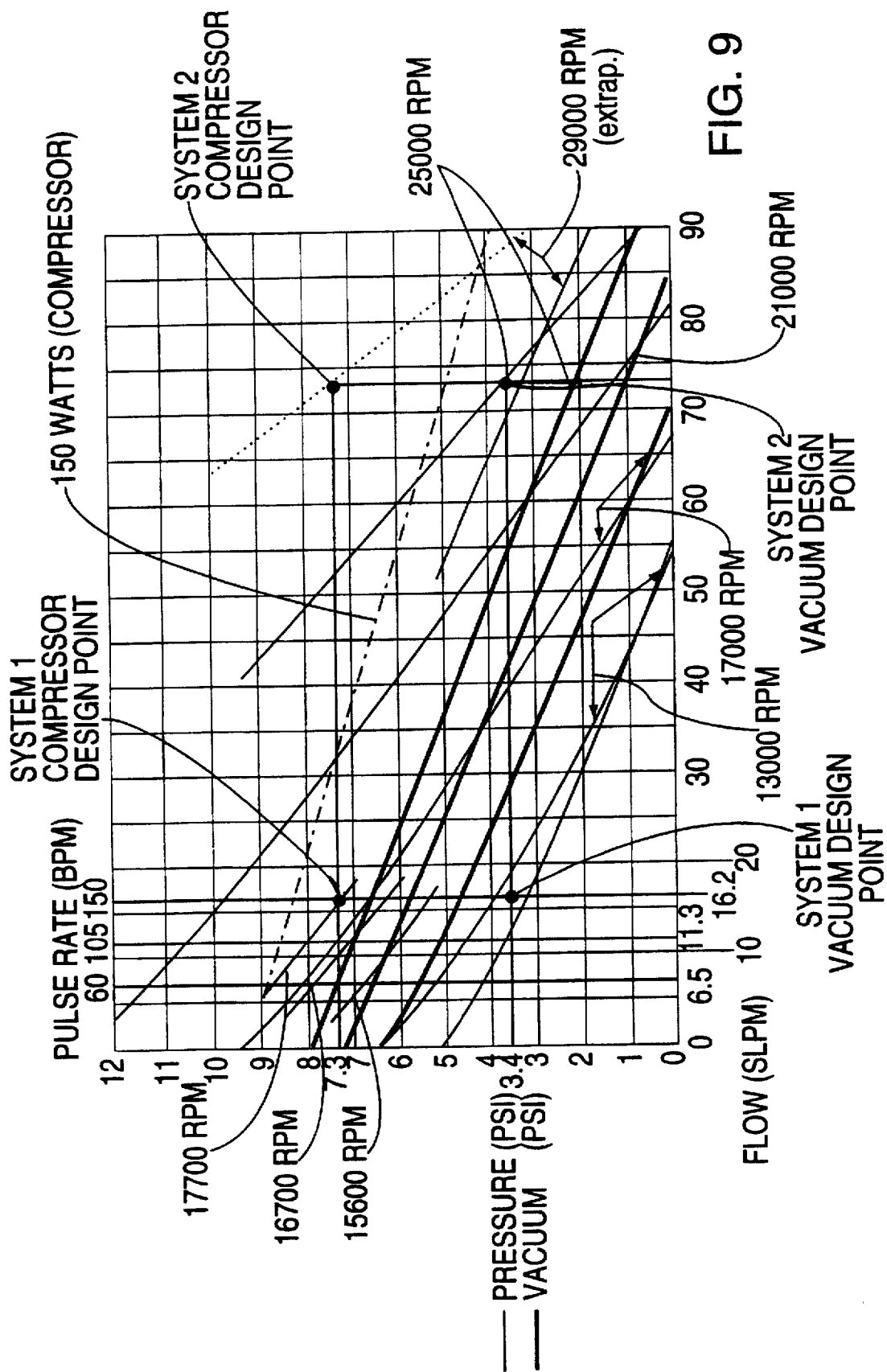
FIG. 9 is a test map showing typical performance of the compressor and vacuum stages of a single rotor drag pump of the design illustrated in FIG. 7.

Approximate inherent regulation of the combined drag compressor/vacuum pump of FIG. 7 can be demonstrated by the performance map shown in FIG. 9.

With operation in the system shown in FIG. 1, and for a 50 ml safety chamber, a 7.3 psig positive driving pressure, and a −3.4 psig driving vacuum, the continuous average flow rates are 16.2 slpm at 150 bpm, 11.3 slpm at 105 bpm and 6.5 slpm at 60 bpm. If the flow rate varies between these limits at the intermediate condition speed of 16.7 Krpm, the driving pressure will vary between 6.58 psig (150 bpm) and 8.05 psig (60 bpm). This shows that there is an inherent pressure regulation of approximately ±10%, so that even without a control, adequate balloon inflation can be maintained. In order for an automatic control to maintain constant pressure, the speed would need to be adjusted between 15.6 krpm and 17.7 krpm, as shown in FIG. 9. The same characteristic applies to vacuum operation except that the self-regulating error band is greater. Speed control of only one quantity (pressure or vacuum) provides a partial correction of the other, where both pressure and vacuum stages are of the same type and connected and driven by the same motor, so that the error of either quantity would not deviate more than ±2 or ±3%.

The feasibility of using a single combined compressor/vacuum pump that is driven by a single motor, rather than using separate pumps driven by two independent motors, depends on the bands within which the single degree-of-freedom motor speed control can maintain both pressure and vacuum. Analysis of the calibration data of the drag compressor/vacuum pump discussed above has indicated that for the change in rotor speed required to maintain a constant pressure within the range of pulse rates, the change in vacuum is within tolerable limits and vice versa. This permits control of only one parameter, either pressure or vacuum, to also maintain the other.

To validate the single degree of freedom control scheme, a pressure control corresponding to the schematic of FIG. 2 was connected into the balloon pump pneumatic system shown in FIG. 1 (without vacuum feedback), and a signal generator was added to manually set the valve drive motor switching rate between 60 bpm and 150 bpm.

The closest balance to the design performance of +7 psig and −3 psig was achieved with a compressor discharge pressure of +6.6 psig and a vacuum pump suction of −2.82 psig.

Figure 10:
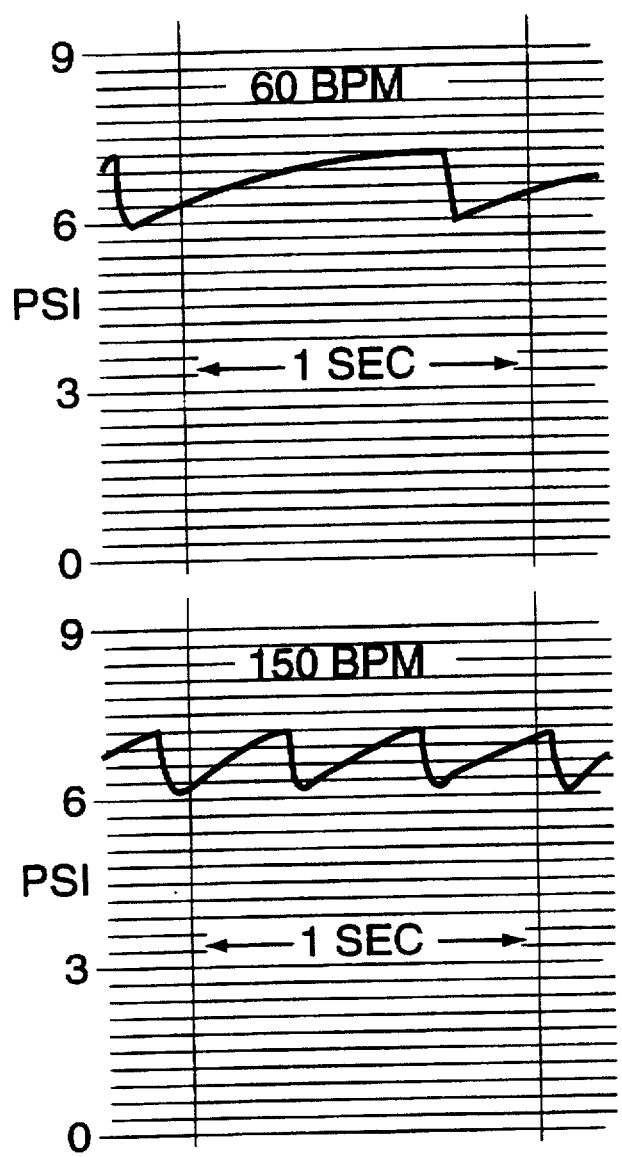
FIG. 10 shows pressure waveshapes at the outlet of the pressure reservoir shown in FIG. 1, under regulation by the control system shown in FIG. 2, at two different valve cycle rates.

The control system was set to give a regulated pressure at the pressure reservoir of 6.6 psi, measured as the peak value of the sawtooth pressure waveshape while the valve was being cycled at 60 bpm, and the resulting pressure signal was fed to an oscillograph recorder. As the valve cycle rate was increased in steps to 150 bpm, the increasing flow from the pressure reservoir created a demand for a greater volume of air, pressure dropped incrementally, and the control system speeded up the compressor motor sufficiently to restore the original peak pressure. The resulting pressure waveshapes for 60 and 150 bpm are shown in FIG. 10, and the regulation of pressure as a function of valve cycle rate appears as a flat horizontal line in FIG. 11. It can be seen that a regulated pressure at a peak value of 6.6 psi is maintained, actually with a variation of +0.9%, −0.3%.

Figure 11:
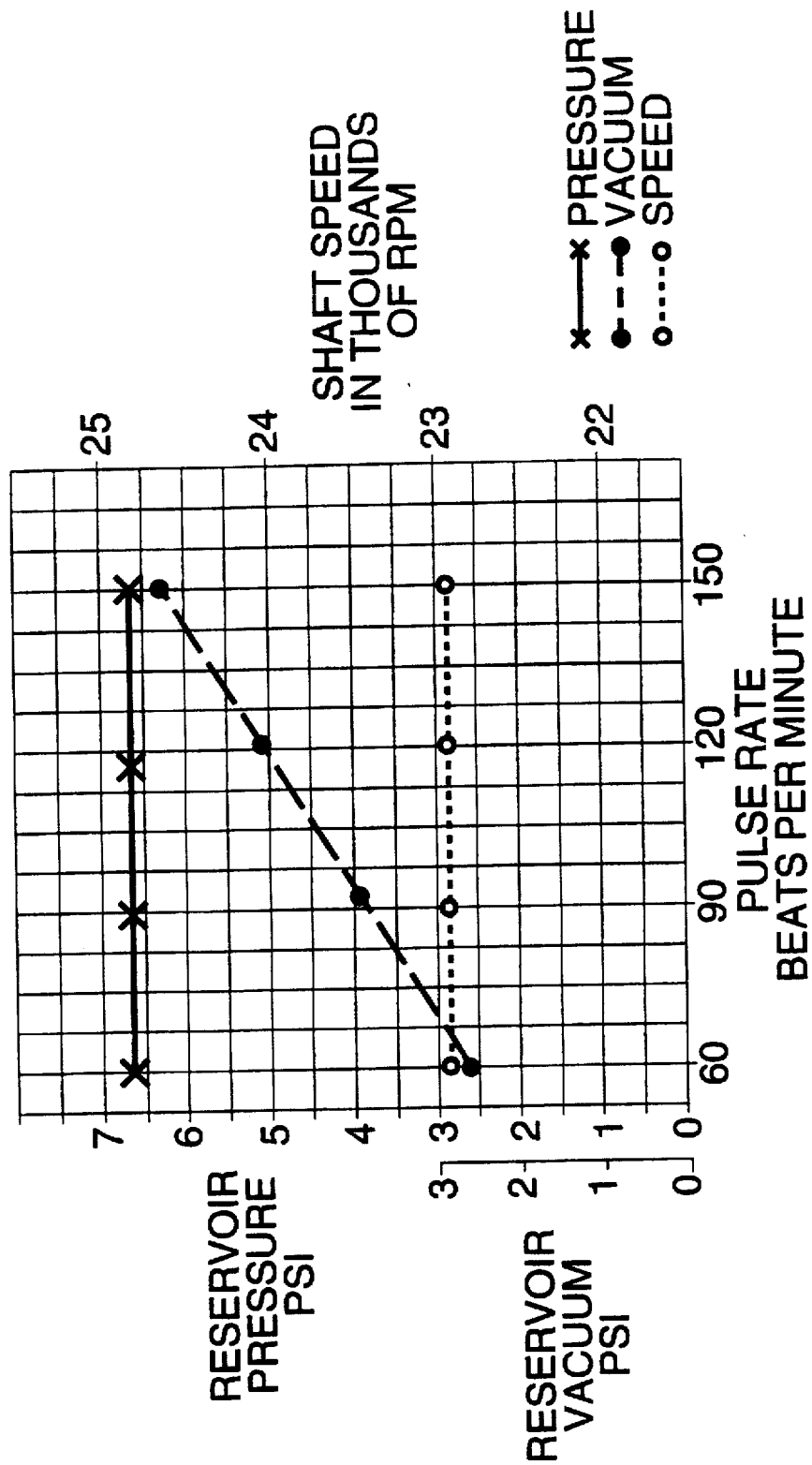
FIG. 11 shows the regulation of both pressure and vacuum in the system of FIG. 1 by a single degree of freedom control, as a function of valve cycle rate.

Of greater significance to the validity of the single degree of freedom control, the pressure in the vacuum reservoir, which started out at −2.82 psi, varied by only +1.8% over the range of pulse rates, as shown in FIG. 11. Over the range of valve pulse rates and shaft speeds of the test, it is seen that the pressures in both the pressure reservoir and the vacuum reservoir remained substantially constant, an excellent demonstration of the tracking of vacuum when the pressure reservoir alone is regulated, a single-shaft compressor/vacuum pump is used, and both have similar characteristics as a function of shaft speed. This feature greatly simplifies the design of a controlled balloon pump driving system and provides validation for the single-pump drive concept.

BACKGROUND REFERENCES

1. Kantrowitz, A., Tjonneland, S., Krakauer, J., Butner, A. N., Phillips, S. J., Yahr, W. Z., Shapiro, M., Freed, P. S., Jaron, D., Sheran, J. L. Jr. *Clinical Experience with Cardiac Assistance by Means of Intraaortic Phase-Shift Balloon Pumping.* Trans Am Soc Artif Intern Organs, Vol. XIV, 1968.
2. Intra-Aortic Balloon Pumps: Evaluation. Health Devices, Vol. 11, No. 1, November, 1981, ECRI, Plymouth Meeting, Pa.
3. Quaal, S. J. *Comprehensive Intra-Aortic Balloon Pumping.* C. V. Mosby Company, 1984.
4. Mulopoulos, S. D., Topaz, S., Kolff, W. J. *Diastolic balloon pumping (with carbon dioxide) in the aorta—a mechanical assistance to the failing circulation* AM Heart J, 63:669–675, 1986.
5. Kantrowitz, A., Freed, P. S., Tachi, H., Suzuki, A. *Intraaortic Balloon Pump Apparatus and Method of Using Same.* U.S. Pat. No. 4,692,148 granted Sep. 8, 1987.
6. Nakamura, T., Hayashi, K., Asada, M., Sakai, K., Tanabe, T. *Electromechanically Driven Computer Controlled Drive System for Intra-Aortic Balloon.* J Int Soc Artif Organs, Vol. 14, Suppl. 1, 1990.
7. Kantrowitz, A., Freed, P. S., Cardona, R. R., Gage, K., Marinescu, G. N., Westveld, A. H., Litch, B., Suzuki, A., Hayakawa, H., Takano, T., Rios, C.E., Rubenfire, M. *Initial Clinical Trial of a Closed Loop, Fully Automatic Intra-aortic Balloon Pump.* ASAIO Journal, 1992.

What is claimed is:

1. A controlled fluid driving system for driving a medical device, comprising:

a fluid load, first means to deliver a fluid under positive pressure to said load, including a pressure pump having an inlet and outlet mounted on a first drive shaft, a pressure line between said pressure pump and said load, and a pressure reservoir in said pressure line, connected to said outlet of said pressure pump, and continuously supplied by said pressure pump, second means to remove said fluid under reduced pressure from said load, including a vacuum pump having a separate inlet and a separate outlet mounted on a second drive shaft, a vacuum line between said vacuum pump and said load, and a vacuum reservoir in said vacuum line, connected to said inlet of said vacuum pump, and continuously evacuated by said vacuum pump, said vacuum pump having a characteristic performance that varies with speed in a manner similar to that of said pressure pump, third means to drive the pressure pump and the vacuum pump at the same drive speed, fourth means for selecting said vacuum line or said pressure line and a value of controlled pressure in one of said lines between one of said pumps and said load, having an output, such that the pressure in the other of said lines will be at a known value within an allowable band, fifth means to measure the actual pressure in said selected line, having an output related to the pressure in said selected line, sixth comparator means to compare said controlled and actual pressure outputs, to provide a differential output related to their difference, and seventh means responsive to said differential output of said comparator means to vary said drive speed in a direction and by an amount to reduce said differential output to a minimum, so as to maintain the pressure in said selected line at its selected value, and the pressure in said other line at a constant value within said allowable band.

2. A controlled fluid driving system as claimed in claim 1, in which a fluid is delivered to said load and removed from said load that is different from said fluid delivered from said pressure pump, and removed by said vacuum pump, and including a fluid isolator connected in series with said load, that contains a flexible element to separate the said two fluids, and to transmit pressure between them.

3. A controlled fluid driving system as claimed in claim 1, in which said fluid delivered to and removed from said load is a gas.

4. A controlled fluid driving system as claimed in claim 1, including valve means to connect said first means to said load while fluid under positive pressure is being delivered, and to connect said second means to said load while fluid under reduced pressure is being removed.

5. A controlled fluid driving system as claimed in claim 1, in which the drive shaft of said pressure pump and said vacuum pump is common.

6. A controlled fluid driving system as claimed in claim 5, in which both pumps are drag pumps and have a common rotor, and their impellers are located on opposite sides of said rotor.

7. A controlled fluid driving system as claimed in claim 1, in which one of said pumps is a drag pump.

8. A controlled fluid driving system as claimed in claim 1, in which said load is a cardiac assist device.

9. A controlled fluid driving system, comprising:

a fluid load, a pressure pump to deliver fluid to said load through a pressure line under positive pressure, a vacuum pump to remove fluid from said load through a vacuum line under reduced pressure, said vacuum pump providing a variation of performance with speed similar to that of said pressure pump, driving means to drive the pressure pump and the vacuum pump at the same speed, means for selecting said vacuum line or said pressure line and a value of controlled pressure in one of said lines between one of said pumps and said load, having an output such that the pressure in the other of said lines will be at a known value within an allowable band, means to measure the actual pressure in said selected line, having an output related to the pressure in said selected line, comparator means to compare said controlled and actual pressure outputs, to provide a differential output related to their difference, means responsive to the differential output, of said means to compare which vary said drive speed in a direction and by an amount to reduce said differential output to a minimum so as to maintain the pressure in said selected line at said selected value, and the pressure in said other line at a constant value within said allowable band.

electrically operated valve means to connect said pressure pump to said load while fluid under positive pressure is being delivered, and to connect said vacuum pump to said load while fluid under reduced pressure is being removed, an electronic control system and valve driver to actuate said valve means, including means to periodically drive said valve means to alternatively connect said positive pressure and said reduced pressure to said load, said periodic driving means being connected to a source of a signal related to an electrocardiogram.

10. A controlled fluid driving system, comprising:

an intra-aortic balloon, a pressure pump to deliver fluid to said balloon through a pressure line under positive pressure, a vacuum pump to remove fluid from said balloon through a vacuum line under reduced pressure, said vacuum pump providing a variation of performance with speed similar to that of said pressure pump, driving means to drive the pressure pump and the vacuum pump at the same speed, means for selecting said vacuum line or said pressure line and a value of controlled pressure in one of said lines between one of said pumps and said balloon having an output such that the pressure in the other of said lines will be at a known value within an allowable band, means to measure the actual pressure in said selected line, having an output related to the pressure in said selected line, comparator means to compare said controlled and actual pressure outputs, to provide a differential output related to their difference, means responsive to the differential outputs, of said means to compare which vary said drive speed in a direction and by an amount to reduce said differential output to a minimum so as to maintain the pressure in said selected line at said selected value, and the pressure in said other line at a constant value within said allowable band.

11. A controlled fluid driving system, comprising:

a fluid load, a pressure pump to deliver fluid to said load through a pressure line under positive pressure, a vacuum pump to remove fluid from said load through a vacuum line under reduced pressure, said vacuum pump providing a variation of performance with speed similar to that of said pressure pump, driving means to drive the pressure pump and the vacuum pump at the same speed, means for selecting said vacuum line or said pressure line a value of controlled pressure in one of said lines between one of said pumps and said load, having an output such that the pressure in the other of said lines will be at a known value within an allowable band, means to measure the actual pressure in said selected line, having an output related to the pressure in said selected line, comparator means to compare said controlled and actual pressure outputs, to provide a differential output related to their difference, means responsive to the differential output, of said means to compare which vary said drive speed in a direction and by an amount to reduce said differential output to a minimum so as to maintain the pressure in said selected line at said selected value, and the pressure in said other line at a constant value within an allowable band, a source of pressure intermediate to said positive pressure and to said reduced pressure, and means to connect said intermediate pressure to said load.

12. A controlled fluid driving system as claimed in claim 11 including valve means to alternately connect said positive pressure and said reduced pressure to said load and additional valve means to momentarily connect said intermediate pressure to said load between said alternate connections to positive pressure and to reduced pressure.

13. A controlled fluid driving system as claimed in claim 11, including valve means to alternately connect said pressure line and said vacuum line to said load, and additional valve means to momentarily connect said source of intermediate pressure to said load between said alternate connections to said pressure line and to said vacuum line.

14. A controlled fluid driving system as claimed in claim 13, including an electronic control system and valve driver to actuate said valve means.

15. A controlled fluid driving system as claimed in claim 14 in which said electronic control system includes means to periodically drive said valve means to alternately connect said first means and said second means to said load.

* * * * *